(12) United States Patent
Cowley

(10) Patent No.: US 10,828,060 B2
(45) Date of Patent: Nov. 10, 2020

(54) HEMOSTAT-STYLE ULTRASONIC SURGICAL INSTRUMENT WITH CLAMP FORCE-LIMITING FEATURE

(71) Applicant: COVIDIEN LP, Mansfield, MA (US)

(72) Inventor: Matthew S. Cowley, Frederick, CO (US)

(73) Assignee: Covidien LP, Mansfield, MA (US)

( * ) Notice: Subject to any disclaimer, the term of this patent is extended or adjusted under 35 U.S.C. 154(b) by 158 days.

(21) Appl. No.: 16/006,954

(22) Filed: Jun. 13, 2018

(65) Prior Publication Data

US 2019/0380734 A1 Dec. 19, 2019

(51) Int. Cl.
*A61B 17/32* (2006.01)
*A61B 90/00* (2016.01)

(52) U.S. Cl.
CPC ...... *A61B 17/320092* (2013.01); *A61B 90/03* (2016.02); *A61B 2017/320074* (2017.08);
(Continued)

(58) Field of Classification Search
CPC ........ A61B 17/320092; A61B 17/2816; A61B 90/03; A61B 2090/034; A61B 2090/032;
(Continued)

(56) References Cited

U.S. PATENT DOCUMENTS

| 4,106,195 A | * | 8/1978 | Berg | ................. | B26B 17/00 30/178 |
| 6,425,907 B1 | | 7/2002 | Shibata et al. | | |

(Continued)

FOREIGN PATENT DOCUMENTS

| CA | 2249748 A1 | 4/1999 |
| EP | 0450608 A1 | 10/1991 |

(Continued)

OTHER PUBLICATIONS

Extended European Search Report issued in corresponding European Application No. 19179628.3 dated Aug. 21, 2019, 10 pages.

(Continued)

*Primary Examiner* — Anh T Dang
(74) *Attorney, Agent, or Firm* — Carter, DeLuca & Farrell LLP

(57) ABSTRACT

An ultrasonic surgical instrument includes a first shaft member, a jaw member extending distally from the first shaft member, a second shaft member, an ultrasonic blade extending distally from the second shaft member and positioned to oppose the jaw member, and a force-limiting hinge assembly operably coupling the shaft members with one another such that movement of the shaft members between a spaced-apart position and an approximated position moves the jaw member and the ultrasonic blade between an open position and a clamping position for clamping tissue therebetween. The force-limiting hinge assembly includes a hinge arm fixedly engaged to one of the shaft members at a first end thereof and pivotably coupled to the other of the shaft members at a second end thereof. The hinge arm is configured to flex to regulate a clamping force applied to tissue clamped between the jaw member and the ultrasonic blade.

20 Claims, 3 Drawing Sheets

(52) U.S. Cl.
CPC ............. *A61B 2017/320082* (2017.08); *A61B 2017/320094* (2017.08); *A61B 2017/320095* (2017.08); *A61B 2090/034* (2016.02)

(58) Field of Classification Search
CPC ....... A61B 2017/320094; A61B 2017/320074; A61B 2017/320082; A61B 2017/322095
See application file for complete search history.

(56) References Cited

U.S. PATENT DOCUMENTS

| | | |
|---|---|---|
| 6,458,142 B1 | 10/2002 | Faller et al. |
| 2006/0079879 A1 | 4/2006 | Faller et al. |
| 2007/0191713 A1 | 8/2007 | Eichmann et al. |
| 2013/0253499 A1 | 9/2013 | Kimball et al. |
| 2013/0296843 A1 | 11/2013 | Boudreaux et al. |
| 2013/0345732 A1* | 12/2013 | Dannaher ...... A61B 17/320092 606/169 |
| 2015/0080925 A1 | 3/2015 | Schulte et al. |
| 2015/0148831 A1* | 5/2015 | Faller ................ A61B 17/2909 606/169 |
| 2016/0175033 A1 | 6/2016 | Le |
| 2017/0196620 A1 | 7/2017 | Jadhav |
| 2017/0224348 A1 | 8/2017 | Wong et al. |

FOREIGN PATENT DOCUMENTS

| | | |
|---|---|---|
| EP | 3281588 A1 | 2/2018 |
| JP | 2009514566 A | 4/2009 |
| JP | 2010167084 A | 8/2010 |
| JP | 2010534522 A | 11/2010 |
| JP | 2013192953 A | 9/2013 |
| JP | 2016538071 A | 12/2016 |

OTHER PUBLICATIONS

Australian Examination Report issued in corresponding Australian Application No. 2019202722 dated Jul. 3, 2019, 7 pages.
Australian Examination Report issued in corresponding Australian Application No. 2019202722 dated Dec. 20, 2019, 4 pages.
First European Examination Report issued in correponding European Application No. 19 179 628.3 dated Aug. 4, 2020, 5 pages.
Canadian Office Action issued in corresponding Canadian Application No. 3,040,369 dated Aug. 18, 2020, 6 pages.
Japanese Notice of Allowance issued in corresponding Japanese Application No. 2019-088227 dated Jun. 5, 2020, 5 pages.

* cited by examiner

HEMOSTAT-STYLE ULTRASONIC SURGICAL INSTRUMENT WITH CLAMP FORCE-LIMITING FEATURE

BACKGROUND

Technical Field

The present disclosure relates to ultrasonic surgical instruments and, more particularly, to a hemostat-style ultrasonic surgical instrument configured to limit clamping force to a maximum clamping force.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, and/or fulgurate tissue to effect hemostasis.

Ultrasonic surgical instruments typically employ a transducer coupled to a handle of the ultrasonic surgical instrument and configured to produce ultrasonic energy for transmission along a waveguide to an end effector of the ultrasonic surgical instrument that is designed to treat tissue with the ultrasonic energy. The transducer may be driven by an ultrasonic generator that is on-board, e.g., on or within the handle of the ultrasonic surgical instrument, or remotely disposed, e.g., as a set-top box connected to the ultrasonic surgical instrument via a surgical cable. The end effector of the ultrasonic surgical instrument may include a blade that receives the ultrasonic energy from the waveguide for application to tissue and a jaw member configured to clamp tissue between the blade and the jaw member to facilitate treatment thereof.

SUMMARY

As used herein, the term "distal" refers to the portion that is described which is further from a user, while the term "proximal" refers to the portion that is described which is closer to a user. Further, any or all of the aspects described herein, to the extent consistent, may be used in conjunction with any or all of the other aspects described herein.

Provided in accordance with aspects of the present disclosure is an ultrasonic surgical instrument including a first shaft member, a jaw member extending distally from the first shaft member, a second shaft member, an ultrasonic blade extending distally from the second shaft member and positioned to oppose the jaw member, and a force-limiting hinge assembly operably coupling the first and second shaft members with one another such that movement of the first and second shaft members relative to one another between a spaced-apart position and an approximated position moves the jaw member and the ultrasonic blade relative to one another between an open position and a clamping position for clamping tissue therebetween. The force-limiting hinge assembly includes a hinge arm fixedly engaged to one of the first or second shaft members at a first end thereof and pivotably coupled to the other of the first or second shaft members at a second end thereof. The hinge arm is configured to flex to regulate a clamping force applied to tissue clamped between the jaw member and the ultrasonic blade.

In an aspect of the present disclosure, the first end of the hinge arm is fixedly engaged with the second shaft member and the second end of the hinge arm is pivotably coupled to the first shaft member.

In another aspect of the present disclosure, the first end of the hinge arm is monolithically formed with the one of the first or second shaft members.

In still another aspect of the present disclosure, a pivot pin pivotably couples the second end of the hinge arm with the other of the first or second shaft members.

In yet another aspect of the present disclosure, the hinge arm is resiliently flexible.

In still yet another aspect of the present disclosure, the jaw member includes a structural body and a tissue pad supported on the structural body.

In another aspect of the present disclosure, a transducer and waveguide assembly is supported by the second shaft member. The transducer and waveguide assembly includes an ultrasonic transducer and an ultrasonic waveguide coupled to and extending distally from the ultrasonic transducer. The ultrasonic blade is defined at a distal end of the ultrasonic waveguide.

In another aspect of the present disclosure, the transducer and waveguide assembly is removable from the second shaft member.

In yet another aspect of the present disclosure, each of the first and second shaft members includes a handle disposed towards a proximal end thereof. The handles are configured to facilitate movement of the first and second shaft members relative to one another between the spaced-apart position and the approximated position.

In still another aspect of the present disclosure, an activation button is disposed on the second shaft member. The activation button is selectively activatable to supply ultrasonic energy to the ultrasonic blade.

In still yet another aspect of the present disclosure, the hinge arm regulates the clamping force applied to tissue clamped between the jaw member and the ultrasonic blade by flexing to inhibit the clamping force from exceeding a maximum clamping force.

Another ultrasonic surgical instrument provided in accordance with aspects of the present disclosure includes a first shaft member including a shaft portion and a jaw member extending distally from the shaft portion, a second shaft member supporting a transducer and waveguide assembly, and a force-limiting hinge assembly. The transducer and waveguide assembly includes an ultrasonic transducer and an ultrasonic waveguide coupled to and extending distally from the ultrasonic transducer. An ultrasonic blade is defined at a distal end of the ultrasonic waveguide and positioned to oppose the jaw member. The force-limiting hinge assembly operably couples the first and second shaft members with one another such that movement of the first and second shaft members relative to one another between a spaced-apart position and an approximated position moves the jaw member and the ultrasonic blade relative to one another between an open position and a clamping position for clamping tissue therebetween. The force-limiting hinge assembly includes a hinge arm fixedly engaged to the second shaft member at a first end thereof and pivotably coupled to the first shaft member at a second end thereof. The hinge arm is configured to flex to regulate a clamping force applied to tissue clamped between the jaw member and the ultrasonic blade. The ultrasonic surgical instrument may further include any of the other aspects and/or features detailed hereinabove or otherwise herein.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements and.

DETAILED DESCRIPTION

Figure 1:
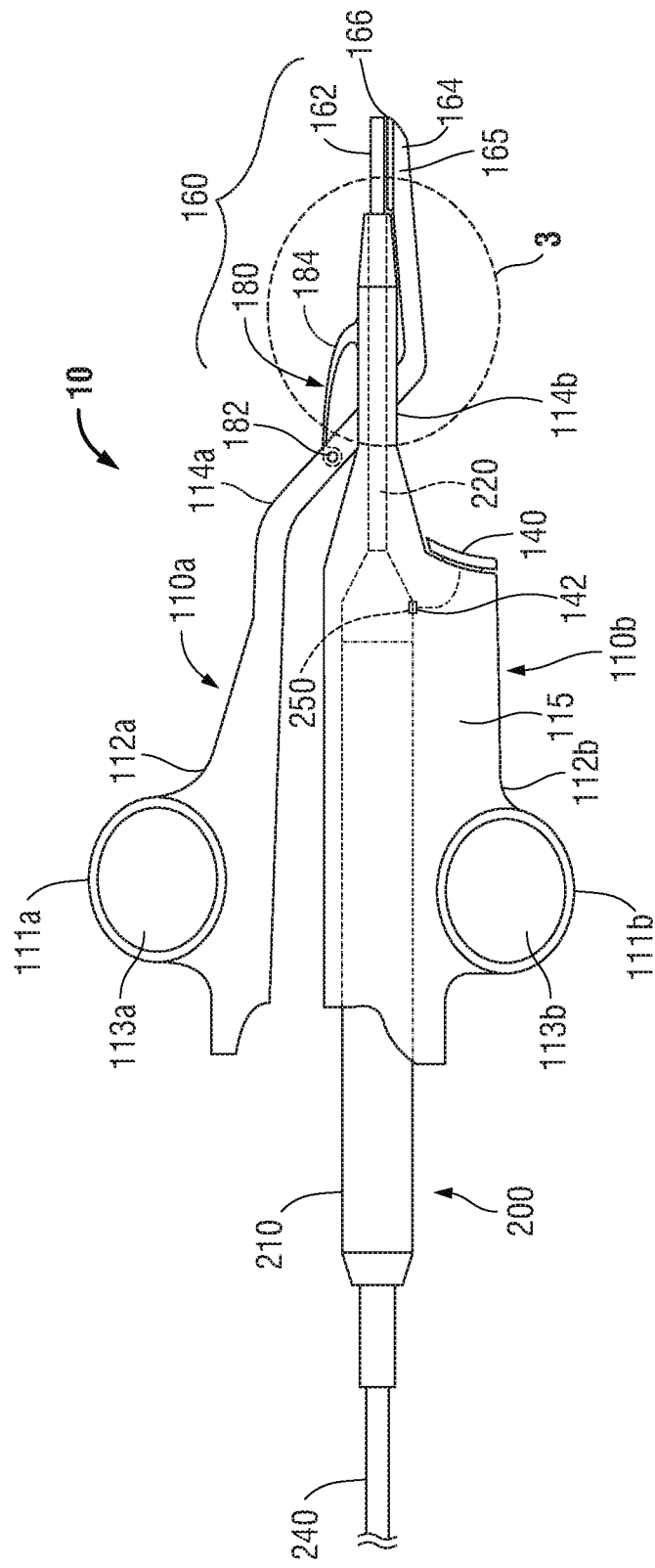
FIG. 1 is a side view of a hemostat-style ultrasonic surgical instrument provided in accordance with the present disclosure.

Referring to FIG. 1, a hemostat-style ultrasonic surgical instrument provided in accordance with the present disclosure is shown generally identified by reference numeral 10. Ultrasonic surgical instrument 10 is configured to operably couple to an ultrasonic surgical generator (not shown) and generally includes two elongated shaft members 110a, 110b, an activation button 140, an end effector assembly 160, a force-limiting hinge assembly 180, and a transducer and waveguide assembly 200.

Each shaft member 110a, 110b includes a handle 111a, 111b disposed towards the proximal end 112a, 112b thereof. Each handle 111a, 111b defines a finger hole 113a, 113b therethrough for receiving a finger of the user. One of the shaft members, e.g., shaft member 110a, includes a jaw member 164 of end effector assembly 160 extending from the distal end 114a thereof. The other shaft member, e.g., shaft member 110b, defines an elongated body 115 configured to receive transducer and waveguide assembly 200 therethrough. Elongated body 115 mounts activation button 140 thereon. Transducer and waveguide assembly 200 may be releasably insertable through elongated body 115 into engagement therewith, or may be permanently affixed within elongated body 115. In either configuration, elongated body 115 is configured to receive and engage transducer and waveguide assembly 200 therein such that blade 162 of transducer and waveguide assembly 200 extends distally from distal end 114b of elongated body 115 and is positioned to oppose jaw member 164 of shaft member 110a. Shaft members 110a, 110b are coupled to one another towards the distal ends 114a, 114b, respectively, thereof via force-limiting hinge assembly 180, as detailed below, to enable jaw member 164 to pivot relative to blade 162 to clamp tissue therebetween.

Figure 2:
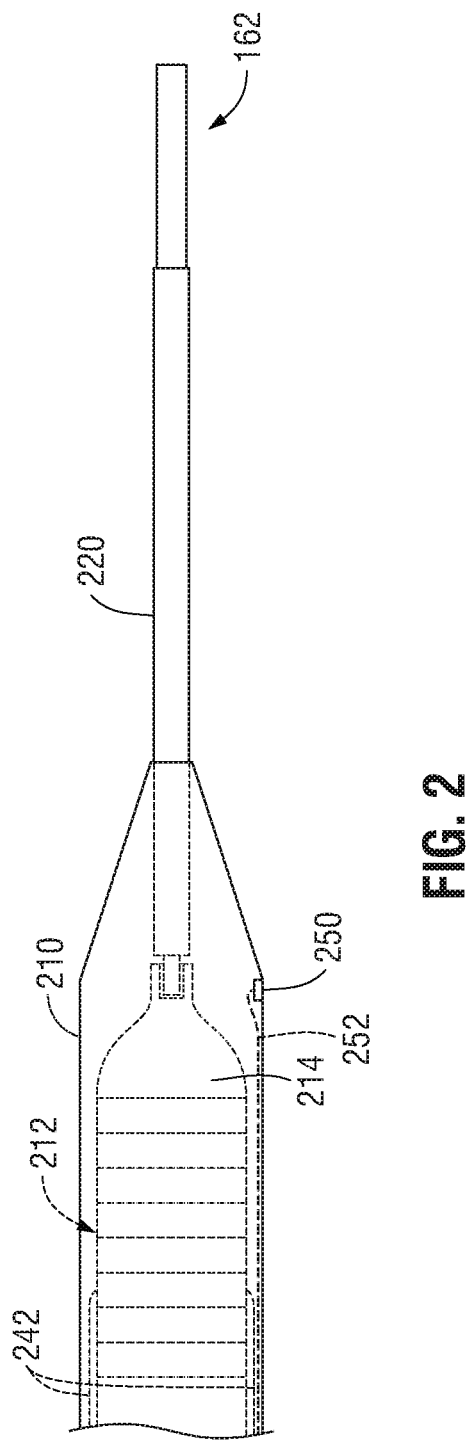
FIG. 2 is an enlarged, side view of a transducer and waveguide assembly of the ultrasonic surgical instrument of FIG. 1.

With reference to FIG. 2, transducer and waveguide assembly 200 includes a housing 210, an ultrasonic transducer 212, e.g., a piezoelectric stack, disposed within housing 210, an ultrasonic horn 214 disposed within housing 210 and coupled to ultrasonic transducer 212, and an ultrasonic waveguide 220 coupled to ultrasonic horn 214, e.g., via a releasable threaded engagement, within housing 210 and extending distally from housing 210 to define an ultrasonic blade 162 of end effector assembly 160 at the distal of ultrasonic waveguide 220, distally-spaced from housing 210. Transducer and waveguide assembly 200 further includes a cable 240 extending proximally from housing 210 to enable connection of transducer and waveguide assembly 200 to an ultrasonic generator (not shown). Alternatively, cable 240 may extend from another suitable location on ultrasonic surgical instrument 10, e.g., handle 111b.

Piezoelectric stack 214 includes a plurality of piezoelectric elements stacked with electrodes disposed therebetween and is configured to convert electrical energy provided by the ultrasonic generator (not shown) and supplied thereto via wires 242 extending through cable 240 (FIG. 1) into mechanical energy that is transmitted to ultrasonic waveguide 220 via ultrasonic horn 214. Ultrasonic waveguide 220, in turn, is configured to transmit the mechanical energy to blade 162 at the distal end of ultrasonic waveguide 220 such that blade 162 oscillates at ultrasonic frequencies.

Referring also to FIG. 1, transducer and waveguide assembly 200 may further include an external contact 250 disposed on housing 210 and electrically coupled to a wire 252 extending through housing 210 and cable 240 to the ultrasonic generator (not shown). Contact 250 is configured to mate with a corresponding contact 142 disposed within elongated body 115 of shaft member 110b and electrically coupled to activation button 140 of ultrasonic surgical instrument 10 to enable the selective activation of ultrasonic surgical instrument 10. Activation button 140, more specifically, may be selectively activatable in a first position and a second position to supply electrical energy from the ultrasonic generator to transducer and waveguide assembly 200 for operating ultrasonic instrument 10 in a low-power mode of operation and a high-power mode of operation, respectively.

Continuing with reference to FIGS. 1 and 2, ultrasonic waveguide 220, as noted above, extends distally from housing 210 and defines blade 162 of end effector assembly 160 at the distal end thereof. Due to the coupling of shaft members 110a, 110b towards the distal ends 114a, 114b, respectively, thereof, via force-limiting hinge assembly 180, handles 111a, 111b may be moved relative to one another to thereby pivot jaw member 164 relative to blade 162 between an open position, wherein jaw member 164 is spaced-apart from blade 162, and a closed position, wherein jaw member 164 is approximated relative to blade 162 in juxtaposed alignment therewith for clamping tissue therebetween.

End effector assembly 160 includes blade 162 and jaw member 164. Blade 162 may define a linear configuration or a curved configuration curved in any direction relative to jaw member 164, for example, such that the distal tip of blade 162 is curved towards jaw member 164, away from jaw member 164, or laterally (in either direction) relative to jaw member 164. Blade 162 may further define a multi-curve configuration wherein blade 162 includes multiple curves and/or is curved in multiple directions.

Jaw member 164 includes a substantially rigid (within material and manufacturing tolerances) structural jaw body 165 which may be monolithically formed with or otherwise engaged to the distal end 114a of shaft member 110a. jaw member 164 further includes a tissue pad 166 supported on structural jaw body 165 and positioned to oppose blade 162. Tissue pad 166 is formed at least partially from a compliant material, e.g., PTFE, and serves to facilitate clamping tissue and maintaining the clamp on tissue when blade 162 is activated. Tissue pad 166 also protects blade 162, structural jaw body 165, and surroundings from damage by inhibiting contact between blade 162 and structural jaw body 165.

Figure 3:
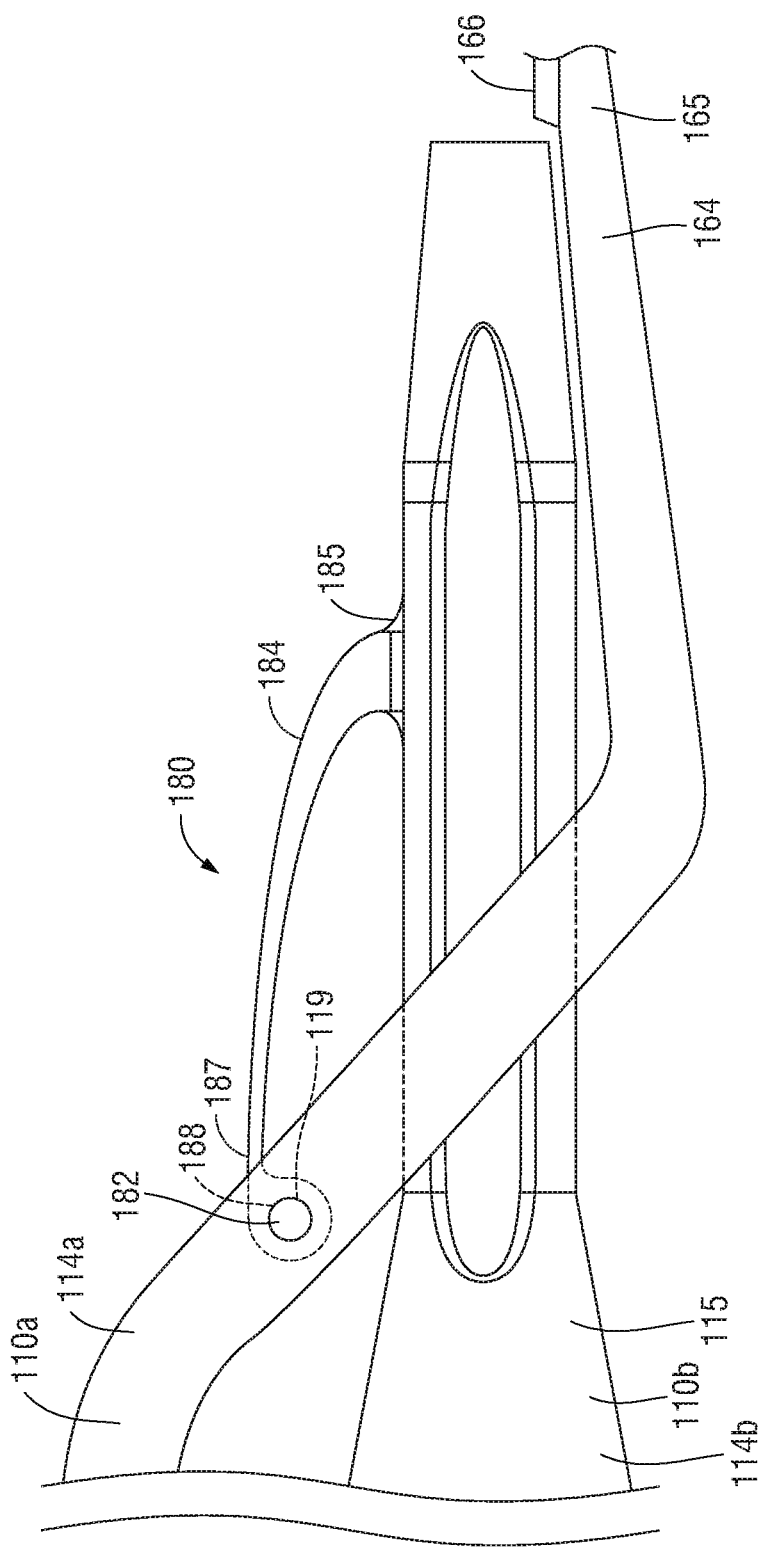
FIG. 3 is an enlarged, side view of the area of detail indicated as "3" in FIG. 1, with the transducer and waveguide assembly removed.

Referring to FIG. 3, in conjunction with FIG. 1, as noted above, first and second shaft members 110a, 110b are coupled to one another towards the distal ends 114a, 114b, respectively, thereof via force-limiting hinge assembly 180. Force-limiting hinge assembly 180 includes a pivot pin 182 and a living hinge arm 184. Living hinge arm 184, as detailed below, is configured to provide a force-limiting feature whereby the clamping force applied to tissue clamped between blade 162 and jaw member 164 is limited to a maximum clamping force. The material forming living hinge arm 184, the length of living hinge arm 184, the shape of living hinge arm 184, the thickness of living hinge arm 184, and/or other factors are tailored to provide a living hinge arm 184 that acts as a constant-force spring to limit the clamping force to a desired maximum clamping force, as detailed below.

Living hinge arm 184 includes a first end portion 185 and a second end portion 187. First end portion 185 of living hinge arm 184 is fixed, e.g., monolithically formed with or otherwise engaged, with one of the shaft members, e.g., elongated body 115 of second shaft member 110*b*, while second end portion 187 of living hinge arm 184 is pivotably coupled to the other of the shaft members, e.g., first shaft member 110*a*, via pivot pin 182. Second end portion 187, more specifically, may be disposed on one side of first shaft member 110*a* or may be received within a slot (not explicitly shown) defined within first shaft member 110*a* such that a pivot aperture 188 defined through second end portion 187 of living hinge arm 184 is aligned with a pivot aperture 119 defined through first shaft member 110*a*. Pivot pin 182 extends through the aligned apertures 119, 188 to pivotably couple second end portion 187 of living hinge arm 184 with first shaft member 110*a*. In this manner, first shaft member 110*a* is movable relative to second shaft member 110*b* about pivot pin 182. More specifically, in response to movement of handles 111*a*, 111*b* of shaft members 110*a*, 110*b*, respectively, towards one another, jaw member 164 is pivoted relative to blade 162 and about pivot pin 182 from an open position, wherein jaw member 164 is spaced-apart from blade 162, to a closed position, wherein jaw member 164 is approximated relative to blade 162 in juxtaposed alignment therewith for clamping tissue therebetween. Notably, although the pivot point, e.g., the location of pivot pin 182, is disposed along first shaft member 110*a*, the pivot point is spaced-apart from second shaft member 110*b*.

In addition to the pivotable movement of first shaft member 110*a* relative to second shaft member 110*b* about pivot pin 182, first shaft member 110*a* is also movable relative to second shaft member 110*b*, independent of the pivoting thereof about pivot pin 182. More specifically, during initial movement of handles 111*a*, 111*b* of shaft members 110*a*, 110*b*, respectively, towards one another to clamp tissue between jaw member 164 and blade 162, the relative motion between shaft members 110*a*, 110*b* is the pivoting thereof about pivot pin 182. However, upon sufficient pivoting of shaft members 110*a*, 110*b* such that jaw member 164 is pivoted sufficiently towards blade 162 to clamp tissue therebetween under the maximum clamping force, further urging of handles 111*a*, 111*b* towards one another does not result in further pivoting of shaft members 110*a*, 110*b* relative to one another but, instead, results in flexion of living hinge arm 184 such that second end portion 187 of living hinge arm 184 is moved relative to first end portion 185 thereof, thereby allowing first shaft member 110*a* to move further towards second shaft member 110*b* without jaw member 164 pivoting further towards blade 162. In this manner, the force-limiting feature is implemented whereby further movement of handles 111*a*, 111*b* towards one another does not result in application of additional clamping force to tissue clamped between jaw member 164 and blade 162.

In use, with tissue clamped between jaw member 164 and blade 162 under the maximum clamping force as detailed above, blade 162 may be activated, e.g., via depression of activation button 140, to supply ultrasonic energy from transducer 212, along waveguide 220, to blade 162. The ultrasonic energy provided at blade 162 is used to treat, e.g., coagulate, cauterize, fuse, seal, cut, desiccate, fulgurate, etc., tissue clamped between jaw member 164 and blade 162. By ensuring the clamping force does not exceed the maximum clamping force, a consistent clamping force can be achieved and, as a result, more reliable tissue treatment can be effected.

While several embodiments of the disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
   a first shaft member;
   a jaw member extending distally from the first shaft member;
   a second shaft member;
   an ultrasonic blade extending distally from the second shaft member and positioned to oppose the jaw member; and
   a force-limiting hinge assembly operably coupling the first and second shaft members with one another such that movement of the first and second shaft members relative to one another between a spaced-apart position and an approximated position moves the jaw member and the ultrasonic blade relative to one another between an open position and a clamping position for clamping tissue therebetween, wherein the force-limiting hinge assembly includes a hinge arm fixedly engaged to one of the first or second shaft members at a first end thereof and pivotably coupled to the other of the first or second shaft members at a second end thereof, the hinge arm configured to flex to regulate a clamping force applied to tissue clamped between the jaw member and the ultrasonic blade.

2. The ultrasonic surgical instrument according to claim 1, wherein the first end of the hinge arm is fixedly engaged with the second shaft member and wherein the second end of the hinge arm is pivotably coupled to the first shaft member.

3. The ultrasonic surgical instrument according to claim 1, wherein the first end of the hinge arm is monolithically formed with the one of the first or second shaft members.

4. The ultrasonic surgical instrument according to claim 1, wherein a pivot pin pivotably couples the second end of the hinge arm with the other of the first or second shaft members.

5. The ultrasonic surgical instrument according to claim 1, wherein the hinge arm is resiliently flexible.

6. The ultrasonic surgical instrument according to claim 1, wherein the jaw member includes a structural body and a tissue pad supported on the structural body.

7. The ultrasonic surgical instrument according to claim 1, further comprising a transducer and waveguide assembly supported by the second shaft member, the transducer and waveguide assembly including an ultrasonic transducer and an ultrasonic waveguide coupled to and extending distally from the ultrasonic transducer, wherein the ultrasonic blade is defined at a distal end of the ultrasonic waveguide.

8. The ultrasonic surgical instrument according to claim 7, wherein the transducer and waveguide assembly is removable from the second shaft member.

9. The ultrasonic surgical instrument according to claim 1, wherein each of the first and second shaft members includes a handle disposed towards a proximal end thereof, the handles configured to facilitate movement of the first and second shaft members relative to one another between the spaced-apart position and the approximated position.

10. The ultrasonic surgical instrument according to claim 1, further comprising an activation button disposed on the second shaft member, the activation button selectively activatable to supply ultrasonic energy to the ultrasonic blade.

11. The ultrasonic surgical instrument according to claim 1, wherein the hinge arm regulates the clamping force applied to tissue clamped between the jaw member and the ultrasonic blade by flexing to inhibit the clamping force from exceeding a maximum clamping force.

12. An ultrasonic surgical instrument, comprising:
a first shaft member including a shaft portion and a jaw member extending distally from the shaft portion;
a second shaft member supporting a transducer and waveguide assembly, the transducer and waveguide assembly including an ultrasonic transducer and an ultrasonic waveguide coupled to and extending distally from the ultrasonic transducer, wherein an ultrasonic blade is defined at a distal end of the ultrasonic waveguide and positioned to oppose the jaw member; and
a force-limiting hinge assembly operably coupling the first and second shaft members with one another such that movement of the first and second shaft members relative to one another between a spaced-apart position and an approximated position moves the jaw member and the ultrasonic blade relative to one another between an open position and a clamping position for clamping tissue therebetween, wherein the force-limiting hinge assembly includes a hinge arm fixedly engaged to the second shaft member at a first end thereof and pivotably coupled to the first shaft member at a second end thereof, the hinge arm configured to flex to regulate a clamping force applied to tissue clamped between the jaw member and the ultrasonic blade.

13. The ultrasonic surgical instrument according to claim 12, wherein the first end of the hinge arm is monolithically formed with the second shaft member.

14. The ultrasonic surgical instrument according to claim 12, wherein a pivot pin pivotably couples the second end of the hinge arm with the first shaft member.

15. The ultrasonic surgical instrument according to claim 12, wherein the hinge arm is resiliently flexible.

16. The ultrasonic surgical instrument according to claim 12, wherein the jaw member includes a structural body and a tissue pad supported on the structural body.

17. The ultrasonic surgical instrument according to claim 12, wherein the transducer and waveguide assembly is removable from the second shaft member.

18. The ultrasonic surgical instrument according to claim 12, wherein each of the first and second shaft members includes a handle disposed towards a proximal end thereof, the handles configured to facilitate movement of the first and second shaft members relative to one another between the spaced-apart position and the approximated position.

19. The ultrasonic surgical instrument according to claim 12, further comprising an activation button disposed on the second shaft member, the activation button selectively activatable to supply ultrasonic energy to the ultrasonic blade.

20. The ultrasonic surgical instrument according to claim 12, wherein the hinge arm regulates the clamping force applied to tissue clamped between the jaw member and the ultrasonic blade by flexing to inhibit the clamping force from exceeding a maximum clamping force.

* * * * *